United States Patent [19]

Briggs

[11] 4,300,574

[45] Nov. 17, 1981

[54] DEVICE FOR MEASURING AND INDICATING CHANGES IN RESISTANCE OF A LIVING BODY

[75] Inventor: James Briggs, Pasadena, Calif.

[73] Assignee: Frank Zurn, Hollywood, Calif.

[21] Appl. No.: 105,395

[22] Filed: Dec. 19, 1979

[51] Int. Cl.³ .............................................. A61B 5/05
[52] U.S. Cl. ...................................... 128/734; 324/62
[58] Field of Search ............... 128/693, 723, 734–735; 320/48; 324/62–65 P, 71R

[56] References Cited

U.S. PATENT DOCUMENTS

| | | | |
|---|---|---|---|
| 3,841,316 | 10/1974 | Meyer | 128/734 |
| 3,980,073 | 9/1976 | Shaw | 324/65 P X |
| 4,016,870 | 4/1977 | Lock | 128/735 |
| 4,112,923 | 9/1978 | Tomacek | 128/734 X |

OTHER PUBLICATIONS

Jacobs, J., "Lie Detector," Elektor (English) vol. 1 No. 7, p. 1143 Nov. 1975.
MacPherson, R. D. et al., "Integrated Circuit Measurement of Skin Conductance", Beh. Res. Meth. & Instr. v. 8, No. 4, pp. 361–364 Aug. 1976.
Zimmer, H. et al., "Non-Polarizing, High Accuracy Skin Resistance Transducer for Digital Conversion", Am. Jrnl. and Electronics Apr.–Jun. 1964 pp. 101–104.

Primary Examiner—Robert W. Michell
Assistant Examiner—Francis J. Jaworski
Attorney, Agent, or Firm—Koda and Androlia

[57] ABSTRACT

A device for measuring and indicating changes in the resistance of a living body including a single battery source, a means for setting a reference voltage level provided across the battery, a unity gain high input impedance and low output impedance buffer amplifier having as its input the reference voltage level, a balanceable resistance bridge having the output of the buffer amplifier applied thereto and having the living body coupled thereto as a part of the bridge, a meter amplifier for amplifying any imbalances in the bridge caused by changes in the resistance of the living body and a meter coupled to the output of the meter amplifier for indicating the changes in resistance of the living body.

11 Claims, 1 Drawing Figure

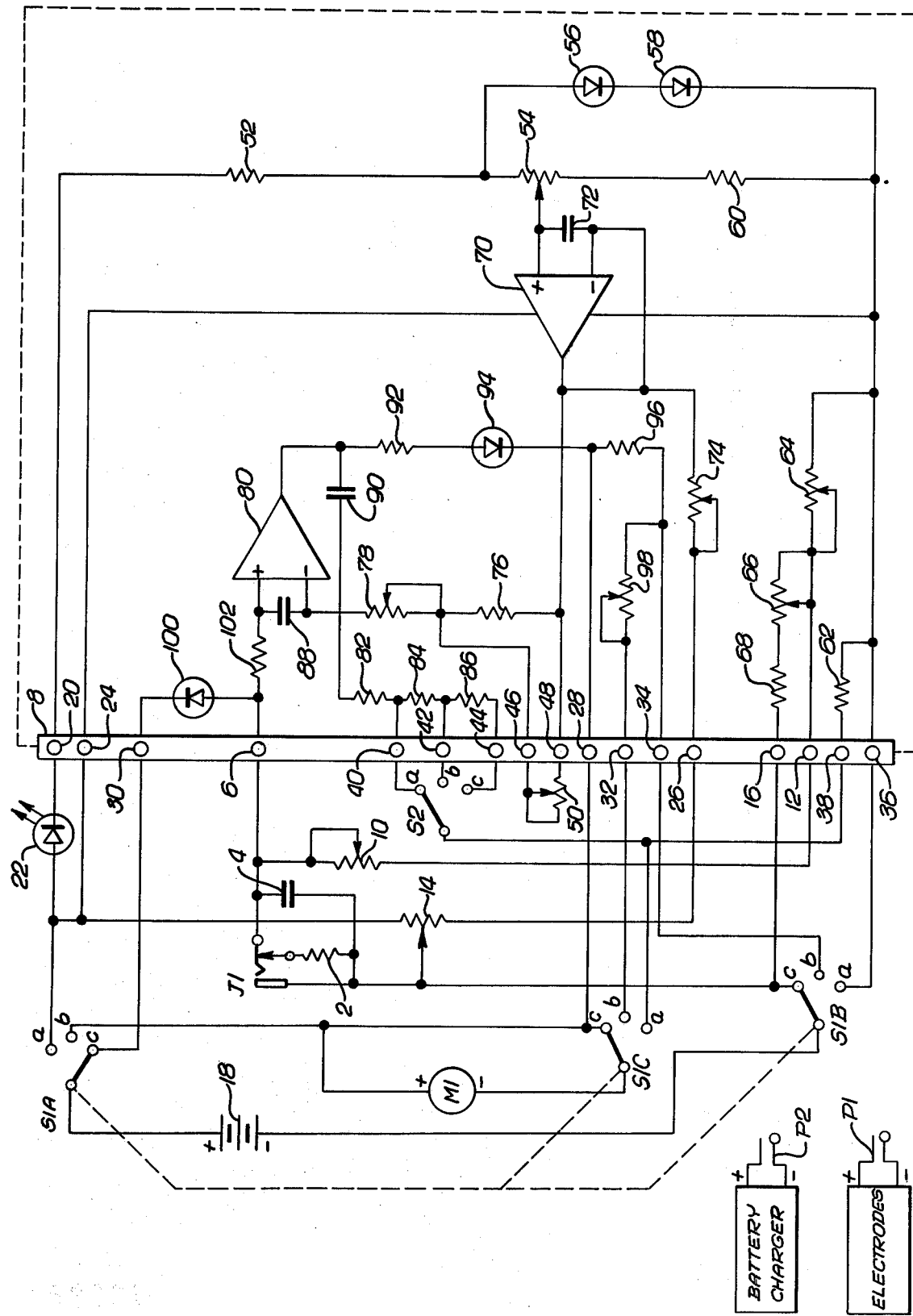

DEVICE FOR MEASURING AND INDICATING CHANGES IN RESISTANCE OF A LIVING BODY

BACKGROUND OF THE INVENTION

1. Field of the Invention

This invention relates to measuring devices for measuring resistance and more particularly to devices for measuring resistance of a living body.

2. Prior Art

In the prior art there exists devices for measuring the resistance of a living body. Such devices are sometimes referred to as galvanic skin response (GSR) devices and are utilized in a variety of applications. Such applications include polygraphs and research uses.

Such instruments contained in the prior art have several drawbacks. Firstly, the better instruments have a high power consumption, are expensive, are very complex to achieve the required stability, are large and non portable and have complex and confusing controls. The less expensive and portable units also have their disadvantages. In particular, such disadvantages including high power consumption, poor stability, low sensitivity, an expensive and complex battery source and to avoid shock hazard a complex battery charger.

SUMMARY OF THE INVENTION

Accordingly, it is a general object of the present invention to provide a device for measuring and indicating changes in the resistance of a living body which has low power consumption, high stability, portability, high sensitivity and simple controls.

It is another object of the present invention to provide a device for measuring and indicating changes in resistance of the living body which is relatively simple and inexpensive.

It is another object of the present invention to provide a device for measuring and indicating changes in resistance of a living body which has a simple and safe battery charger.

In keeping with the principles of the present invention, the objects are accomplished by a unique device for measuring and indicating changes in resistance of a living body. The device generally includes a highly stable reference voltage source supplying a reference voltage to a balanceable resistance bridge wherein the living body is one portion of the resistance bridge and an amplifier for amplifying any imbalances which occur in the resistance bridge and for supplying an amplified signal to an indicating meter. The highly stable reference voltage is accomplished by providing at least one diode across a battery and utilizing the voltage across the diode an an input to a unity gain buffer-amplifier. The buffer amplifier is an operational amplifier with high input and low output impedances. The ordinary diode is utilized to set the stable reference voltage instead of a zener diode in order to reduce the cost. In addition, in the voltage loop including the diode, a light emitting diode is provided so that the operational condition of the instrument can be determined and providing the light emitting diode in this manner reduces power consumption. Furthermore, to reduce the size and increase the portability, integrated circuits are utilized for the buffer amplifier and the bridge imbalance amplifier.

The device of the present invention further includes a charging circuit which has a high degree of safety for the utilizer of the present device. In particular, the charging circuit is arranged and configured such that the same jack into which the electrodes which are utilized to sense the changes in resistance of the living body are plugged is the same jack into which the charger for the battery of the device is plugged. Therefore, in order to charge the device of the present invention, the plug for the electrodes must first be removed and then the plug of the charger inserted. Therefore, it is not possible to provide charging current onto the electrodes and present a hazardous situation for the user.

BRIEF DESCRIPTION OF THE DRAWING

The above-mentioned features and objects of the present invention will become more apparent in relation to the following description taken in conjunction with the following drawing wherein like reference numerals denote like elements and in which the drawing shows a circuit diagram of a device for measuring and indicating changes in the resistance of the living body in accordance with the teachings of the present invention.

DETAILED DESCRIPTION OF THE INVENTION

Referring to the Figure shown therein is a circuit diagram of a device for measuring and indicating the resistance of the living body in accordance with the teachings of the present invention. In the Figure the device includes an ungrounded normally closed jack J1. Across the jack J1 is connected in parallel a resistor 2 and a capacitor 4. The resistor 2 is coupled to the normally closed jack J1 such that when the plug is inserted into the jack J1, the resistor 2 is disconnected from across the jack J1. The tip of the jack J1 is connected to terminal 6 of terminal board 8 and is further connected via a variable resistor 10 to terminal 12 of the terminal board 8.

The ring contact of the jack J1 is coupled to the wiper of variable resistor 14, contact c of switch section S1B of multi-gang switch S1 and to terminal 16 of terminal board 8. The plus and minus sides of the battery 18 are respectively coupled to the movable contacts of switch sections S1A and S1B of multi-gang switch S1. Contact a of switch section S1A is coupled to terminal 20 of terminal board 8 via light emitting diode 22, to terminal 24 of terminal board 8 and to terminal 26 of terminal board 8 via resistor 14.

Contact b of switch section S1A is connected to the positive terminal of meter M1, to contact c of switch section S1C and to terminal 28 of terminal board 8. The negative terminal of meter M1 is connected to the movable contact of switch section S1C.

Contact c of switch section S1A is coupled to terminal 30 of terminal board 8 while contacts b of switch section S1C, b of switch section S1B and a of switch section S1B are coupled respectively to terminals 32, 34 and 36 of terminal board 8. Contact c of switch section S1C is coupled to terminal 38 of terminal board 8 and to the movable contact of switch S2.

Contacts a, b and c of switch S2 are coupled respectively to terminals 42 and 44 of terminal board 8. Furthermore, coupled across terminals 46 and 48 of terminal board 8 is a variable resistor 50.

Terminal 20 is coupled via resistor 52 to one side of variable resistor 54 and to terminal 36 via the series connected diodes 56 and 58. The other side of variable resistor 54 is coupled to terminal 36 via resistor 60. Terminal 36 is further coupled to terminal 38 via resistor 62, to terminal 12 via variable resistor 64 and to terminal 16 via the series connection of variable resistor 64, variable resistor 66 and fixed resistor 68.

The wiper of variable resistor 54 is coupled to the plus input of operational amplifier 70 and a capacitor 72 is coupled between the plus and minus inputs of operational amplifier 70. The minus input of operational amplifier 70 is further connected to the output of the operational amplifier 70 and is also coupled to terminal 26 via variable resistor 74. The output of operational amplifier 70 is also coupled to terminal 48 and to terminal 46 via fixed resistor 76. Terminal 46 is also coupled via variable resistor 78 to the minus input of operational amplifier 80, to terminal 40 via fixed resistor 82, to terminal 42 via series combination of fixed resistors 82 and 84 and to terminal 44 via the series connection of resistors 82, 84 and 86. The minus input of operational amplifier 80 is further connected to the plus input and the output of operational amplifier 80 via capacitors 88 and 90 respectively.

The series connection of a resistor 92 and a diode 94 coupled the output of operational amplifier 80 to terminal 28 of terminal board 8. In addition, terminal 28 is coupled to terminal 34 via resistor 96 and to terminal 32 via the series connection of resistor 96 and variable resistor 98. A diode 100 is coupled between terminals 6 and 30 and terminal 6 is further coupled to the plus input of operational amplifier 80 via resistor 102.

In practice, the operational amplifiers 70 and 80 may be any high gain, high input impedance operational amplifier such as a National Semiconductor LM358. In addition, the resistor 2 should be a high precision resistor. Also, the diodes 56 and 58 should preferably have forward junction voltages greater than or equal to 0.5 volts and such a diode is a 1N914. Furthermore, that portion of the circuitry which is enclosed within the dotted lines can be provided on a printed circuit board while the remainder of the elements such as the switches, meter and jack may be provided on a front panel and connected to the printed circuit board via a wiring harness.

In operation when the switch S1 is in a position such that the moving contacts of the various switch sections are coupled to contact c, the device is in the OFF/-CHARGE position. In this position the battery is disconnected from the circuitry and a short is applied to the meter M1. Therefore, the device is off. However, the device can also be charged in this position.

If the switch S1 is then moved such that the movable contacts of each of the switch sections S1A, S1B and S1C are coupled to the b contact, the device is in the test position. In this position the voltage of the battery 18 is applied across the meter M1 and a determination can be made that the battery 18 is of sufficient voltage.

If the movable contact of the switch S1 is then moved such that the movable contacts of each section S1A, S1B and S1C are coupled to the a contact, the device is on. With the switch S1 in this position, the device can be used to measure and indicate changes in body resistance. In particular, in this position a voltage is supplied from battery 18 through light emitting diode 22 and resistor 52 to the parallel connection of diodes 56 and 58 and variable resistor 54 and resistor 60. As a result, the total battery voltage appears acrossed light emitting diode 22, resistor 52 and series connection of diodes 56 and 58. As a result, the light emitting diode 22 is turned on and emits light as a result of current flowing through light emitting diode 22, resistor 52 and diodes 56 and 58. Furthermore, a voltage equal to the sum of the junction voltages of the diodes 56 and 58 is established across the diodes 56 and 58. In this manner, a reference voltage can be established utilizing inexpensive diodes. In addition, since the current flowing through the diodes 56 and 58 also flows through light emitting diode 52 to generate light, a simple ON indication can be given by the light emitting diode 52 which does not substantially increase the power consumption of the device.

Utilizing the variable resistor 54, the input voltage to the operational amplifier 70 can be set at some reference level such as one volt. This reference level is less than or equal to the sum of the junction voltages of the diodes 56 and 58. The operational amplifier 70 is arranged such that it is a high input impedance, and low output impedance amplifier with a unity gain. Therefore, if a one volt reference voltage is applied to the input of the operational amplifier 70, a one volt reference voltage appears at the output. As a result, the operational amplifier 70 acts as a buffer stage and provides a very stable output reference voltage level.

The output reference level from the buffer is then supplied to a bridge circuit. The bridge circuit includes resistors 10, 14, 64, 66, 68 and 74. Furthermore, when plug P1 is plugged in to jack J1 resistor 2 is disconnected from across jack J1 and the electrodes coupled to plug P1 are connected to the device. If a living body is then coupled to the electrodes, the resistance of the living body will be coupled to the device. This resistance of the living body also forms parts of the bridge circuit. Therefore, if the bridge circuit is balanced and the resistance of the living body changes, the bridge will become imbalanced resulting in some change of voltage. This change of voltage is applied to the plus input of the operational amplifier 80.

The operational amplifier 80 together with its associated circuit elements form a meter driving circuit. The meter driving circuit substantially comprises operational amplifier 80 together with resistors 50, 76, 78, 82, 84, 86 and 102 and capacitors 88 and 90. This meter driving circuit is essentially a current source for supplying undamped current and the feedback in the meter driving circuit is proportional to the current flowing in the meter. As a result, this type of meter driving circuit supplies an output signal to the meter M1 which quickly varies in response to the input of the operational amplifier 80 and therefore, provides the required sensitivity. In addition, in this meter driving circuit the resistors 82, 84 and 86 together with switch S2 form a gain selection means and by switching switch S2 from contact a to contact b to contact c varies the gain of the meter driving circuit. In addition, by varying resistors 50 and 78, the sensitivity of the meter driving circuit can be adjusted. Furthermore, to eliminate the effects of radio frequency radiation and 60 cycle alternating current, low pass filters consisting of resistor 102 and capacitor 88 and capacitor 90 are provided. The capacitor 90 essentially provides a low pass circuit which eliminates the 60 cycle AC signal while the resistor 102 and capacitor 88 provide low pass filter which substantially eliminates radio frequency signals.

To check the calibration of the device of the present invention, the plug P1 is first removed from the jack J1. This causes the normally closed jack J1 to close and apply the calibration resistor 2 as part of the resistance bridge instead of the living body via the electrodes coupled to plug P1. The calibration resistance 2 is of a predetermined value and of a high precision. In practice, the resistor 2 is a 5,000 Ohm, 0.1 percent resistor. In addition to the resistor 2, a resistor 62 is provided so as to provide a nominal reference position for the needle of the meter M1. Typically, the resistor 62 is set such that the meter M1 reads about ⅓ full scale.

To charge the device of the present invention, the plug P1 is removed from the jack J1. The plug P2 connected to the charger is then inserted into the jack J1. The switch S1 is then placed such that the movable contact of each section S1A, S1B and S1C contacts the c contact. This is the so called OFF/CHARGE position. And the charger is then turned on and the battery 18 is recharged. It should be apparent that utilizing this system wherein the same jack J1 is utilized for both the electrode plug P1 and the charger plug P2 that it is impossible for charging current to be applied to the electrodes which are to be connected to a living body. In this manner, safety during charging of the present device is greatly enhanced.

It should be apparent to those skilled in the art that the above described embodiment is merely illustrative of but one of the many possible specific embodiments which represent the applications of the principles of the present invention. Numerous and varied other arrangements can be readily devised by those skilled in the art without departing from the spirit and scope of the invention.

I claim:

1. A device for measuring and indicating the changes in resistance of a living body comprising:
   a single battery;
   a means for setting a reference voltage level provided across the battery;
   a unity gain high input impedance and low output impedance buffer amplifier having as its input the reference voltage level;
   a balanceable resistance bridge having the output of the buffer amplifier applied thereto, said bridge being arranged such that the living body is coupable thereto as part of said bridge;
   a meter amplifier for amplifying any imbalances in the bridge caused by changes in the resistance of a living body when said living body is coupled thereto; and
   a meter coupled to the output of the meter amplifier for indicating the changes in resistance of the living body when said living body is coupled to said bridge.

2. A device according to claim 1 wherein said means for setting a reference voltage level comprises at least one ordinary diode.

3. A device according to claim 2 wherein a light emitting diode for indicating that said device is on is provided in series with said ordinary diode.

4. A device according to claim 3 wherein said single battery source not only provides said reference voltage level but also powers said buffer amplifier and said meter amplifier.

5. A device according to claim 4 wherein said meter amplifier comprises an operational amplifier having a feedback circuit such that the feedback is proportional to current in said meter and said amplifier acts as an undamped current source.

6. A device according to claim 5, wherein said living body is couplable to said bridge via a jack electrically coupled to said bridge and a plug for insertion into said jack, said plug being coupled to electrodes for coupling said living body to said plug.

7. A device according to claim 6 wherein said jack is a normally closed jack and a calibration resistor is coupled to said jack such that when said plug is removed from said jack, said calibration resistor is coupled to said bridge.

8. A device according to claim 7 further comprising a multi position switch means for turning said device on and off and for connecting said battery to said meter such that the condition of said battery can be read on said meter.

9. A device according to claim 8 further comprising a battery charging means, said battery charging means comprising a battery charger coupled to a charging plug inserted into said jack after said plug coupled to said electrodes is removed and said multi-position switch means is in an off position.

10. A device for measuring and indicating the changes in resistance of a living body comprising:
    a single battery;
    a resistive means for setting a reference level provided across said battery;
    a unity gain high input impedance and low outputed impedence buffer amplifier having as its input the reference voltage level, said buffer amplifier comprising an operational amplifier;
    a balanceable resistance bridge having the output of said buffer amplifier applied thereto, said bridge being arranged such that the living body is coupleable thereto as part of said bridge;
    a female jack electrically coupled to said bridge and a male plug for insertion into said jack, said plug being coupled to electrodes for coupling said living body to said plug;
    a calibration resistor coupled to said jack such that when said plug is removed from said jack, said calibration resistor is coupled to said bridge;
    a meter amplifier for amplifying any imbalances in the bridge caused by changes in the resistance of a living body when said living body is coupled thereto, said meter amplifier being powered by said single battery and comprising an operational amplifier having a feedback circuit such that the feedback is proportional to current in a meter and said amplifier acts as an undamped current source; and
    a meter coupled to the output of the meter amplifier for indicating changes in resistance of the living body when said living body is coupled to said bridge.

11. A device according to claim 10 further comprising a battery charging means comprising a battery charger coupled to a charging plug inserted into said jack after said plug coupled to said electrodes is removed from said jack.

* * * * *